United States Patent
Mercier

(10) Patent No.: US 10,201,161 B2
(45) Date of Patent: Feb. 12, 2019

(54) MOLLUSCICIDAL PARTICLE, BAIT AND METHOD OF CONTROLLING HARMFUL MOLLUSCS

(71) Applicant: DE SANGOSSE, Pont-du-Casse (FR)

(72) Inventor: Frederic Mercier, Montagnac-sur-Auvignon (FR)

(73) Assignee: DE SANGOSSE, Pont-du-Casse (FR)

( * ) Notice: Subject to any disclaimer, the term of this patent is extended or adjusted under 35 U.S.C. 154(b) by 0 days.

(21) Appl. No.: 15/120,595

(22) PCT Filed: Feb. 19, 2015

(86) PCT No.: PCT/EP2015/053510
§ 371 (c)(1),
(2) Date: Aug. 22, 2016

(87) PCT Pub. No.: WO2015/132076
PCT Pub. Date: Sep. 11, 2015

(65) Prior Publication Data
US 2017/0006875 A1   Jan. 12, 2017

(30) Foreign Application Priority Data

Mar. 5, 2014  (FR) .................................. 14 51775

(51) Int. Cl.
| | |
|---|---|
| *A01N 59/16* | (2006.01) |
| *A01N 25/00* | (2006.01) |
| *A01N 25/08* | (2006.01) |
| *A01N 25/26* | (2006.01) |

(52) U.S. Cl.
CPC ........... *A01N 59/16* (2013.01); *A01N 25/008* (2013.01); *A01N 25/08* (2013.01); *A01N 25/26* (2013.01)

(58) Field of Classification Search
CPC ...... A01N 59/16; A01N 25/008; A01N 25/08; A01N 25/26
See application file for complete search history.

(56) References Cited

U.S. PATENT DOCUMENTS

| 4,765,979 | A | * | 8/1988 | Nielsen | .................. | A01N 59/16 |
| | | | | | | 424/682 |
| 6,093,416 | A | * | 7/2000 | Young | .................. | A01N 25/008 |
| | | | | | | 424/405 |
| 6,703,036 | B1 | * | 3/2004 | Young | .................. | A01N 25/008 |
| | | | | | | 424/405 |
| 7,964,205 | B2 | | 6/2011 | Parker et al. | | |
| 2002/0155139 | A1 | * | 10/2002 | Feiler | .................. | A01N 25/008 |
| | | | | | | 424/405 |
| 2007/0148203 | A1 | * | 6/2007 | Parker | .................. | A01N 25/008 |
| | | | | | | 424/410 |

FOREIGN PATENT DOCUMENTS

| WO | 97/26789 A1 | 7/1997 |
| WO | 99/39576 A1 | 8/1999 |

OTHER PUBLICATIONS

C. Salvio, et al, The Efficacy of Three Metaldehyde Pellets Marketed in Argentina, on the Control of Dereoceras reticulatum (Müller) (Pulmonata: Stylommatophora), 6 Span. J Agricul. Res. 70, 76 (Year: 2008).*
I.F. Henderson, et al, Improving Slug Baits: The Effects of Some Phagostimulatns and Molluscicides on Ingestion by the Slug, Dereoceras reticulatum (Müller) (Pulmonata: Limacidae), 121 Ann. Appl. Biol. (Year: 1992).*
Marilyn Wedgwood & Stuart E.R. Bailey, The Inhibitory Effects of the Molluscicide Metaldehyde on Feeding, Locomotion and Faecal Elimination of Three Pest Species of Terrestrial Slug, 112 Ann. Appl. Biol. 439, 450-56 (Year: 1988).*
Stuart E.R. Bailey, Molluscicidal Baits for Control of Terrestrial Gastropods, in Molluscs as Crop Pests G.M. Barker, ed., CABI (Year : 2002).*
International Search Report, dated May 6, 2015, from corresponding PCT application.

* cited by examiner

*Primary Examiner* — Sean M Basquill
(74) *Attorney, Agent, or Firm* — Young & Thompson

(57) ABSTRACT

A molluscicidal particle formed of a solid including at least one metallic compound, including at least one metal selected from the group formed by iron, copper, zinc and aluminum, the solid being suitable for use as an ingested poison for harmful molluscs. The solid includes metaldehyde in a proportion which can vary towards the interior of the solid.

11 Claims, No Drawings

MOLLUSCICIDAL PARTICLE, BAIT AND METHOD OF CONTROLLING HARMFUL MOLLUSCS

The invention relates to a particle, named a molluscicidal particle, of ingested poison for harmful molluscs. The invention also covers a molluscicidal bait comprising at least one molluscicidal particle, especially a molluscicidal bait in divided form comprising molluscicidal particles according to the invention and a process for controlling harmful molluscs in which such molluscicidal particles or such a molluscicidal bait are used.

Such a molluscicidal particle and such a molluscicidal bait find industrial applications in the agricultural field in which solutions are sought for protecting agricultural or non-agricultural plant productions (for example ornamental and amateur gardening productions) against damage caused by harmful molluscs.

Baits directed to controlling harmful molluscs, provided to the harmful molluscs and spread in plant crops, are already known.

In particular, WO 99/39576 discloses a molluscicidal bait comprising iron phosphate, a stabilizer for this bait chosen from the group formed by ethylenediaminedisuccinic acid (EDDS), isomers thereof, salts thereof, metal complexes of ethylenediaminedisuccinic acid and mixtures thereof and a material that is edible to molluscs. According to WO 99/39576, such a composition may comprise a coactive molluscicidal agent which may be metaldehyde.

In practice, commercial preparations based on iron phosphate have authorized application doses of between 7 kg/ha for an agricultural preparation based on 3% iron phosphate, i.e. 100 g of active material per hectare of crop, and 50 kg/ha for a preparation intended for amateur gardening use based on 1% iron phosphate, i.e. 500 g of active material per hectare.

The invention is directed to a molluscicidal particle for reducing the amount of bait to be spread onto plants or crops that is required to obtain protection of the plants and crops against molluscs, especially against harmful molluscs. The invention is also directed to such a molluscicidal particle for reducing the amount of molluscicidal active material spread per hectare of crop to obtain such protection.

The invention is directed to such a molluscicidal particle for also improving the molluscicidal efficacy of particles of WO 99/39576 against harmful molluscs and comprising a simple metallic compound, a chelating agent for stabilizing the metallic compound and, where appropriate, a coactive agent.

The invention is directed to such a molluscicidal particle allowing such an improvement in the efficacy of molluscicidal particles and baits for a reduced amount of particles or bait ingested by the harmful molluscs.

The invention is thus directed to such a poison particle, a bait comprising such particles and such a process which are active on harmful molluscs, while at the same time being more environmentally friendly.

The invention is thus directed to obtaining improved molluscicidal efficacy, especially relative to that of the baits of WO 99/39576. In particular, the invention is directed to obtaining improved molluscicidal efficacy relative to the efficacy of baits comprising about 3% by mass of ferric iron phosphate.

In particular, the invention is directed to proposing such a molluscicidal particle and a molluscicidal bait comprising at least one such molluscicidal particle, especially a plurality of molluscicidal particles, which are suitable for acting rapidly on harmful molluscs and for affording rapid protection of crops against said harmful molluscs.

The invention is also directed to proposing such a molluscicidal particle and a molluscicidal bait that are capable of killing harmful molluscs more rapidly, especially after 3 to 4 days of consumption of said particle, in comparison with known molluscicidal particles. The invention is thus directed to proposing such a molluscicidal particle and a molluscicidal bait with a rapid protective effect on plants and crops.

The invention is thus directed to proposing such a molluscicidal particle and such a molluscicidal bait that are consumed by each harmful mollusc in low amount but for a crop protection efficacy that nevertheless remains high, or even higher than the protection afforded by known baits comprising a simple metallic compound, a stabilizer and, where appropriate, a coactive agent for controlling harmful molluscs.

The invention is also directed to proposing such a molluscicidal particle and a molluscicidal bait for controlling harmful molluscs.

The invention is also directed to proposing such a molluscicidal particle and a molluscicidal bait for the long-lasting and continued protection of plants and/or plant crops against these harmful molluscs.

The invention is also and more particularly directed to proposing such a molluscicidal particle and a molluscicidal bait that are compatible with the usual constraints for the manufacture, storage, conservation and application of known baits for controlling harmful molluscs.

To do this, the invention relates to a molluscicidal particle formed from a solid comprising at least one compound, named a metallic compound, comprising at least one metal chosen from the group formed by iron, copper, zinc and aluminium, said solid being suitable for use as an ingested poison for harmful molluscs, characterized in that the solid comprises metaldehyde in a proportion that varies towards the interior of said solid.

Throughout the text, the term "molluscicidal" qualifies the property of a particle according to the invention, of a solid or of a bait for killing molluscs, especially harmful molluscs, by ingestion.

Metaldehyde is the CAS (Chemical Abstracts Service) chemical compound No. 108-62-3 having the following formula:

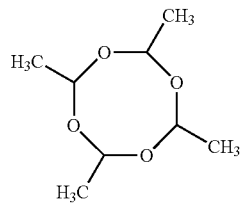

The invention thus relates to a molluscicidal particle (and a molluscicidal bait comprising such a particle) formed from a solid comprising at least one metallic compound and metaldehyde distributed in the solid with a gradient (positive or negative) of metaldehyde directed towards the interior of the solid so as to maintain molluscicidal efficacy for a reduced amount of consumed active material. The invention thus relates to a molluscicidal particle of improved efficacy.

Advantageously and according to the invention, the proportion of metaldehyde varies towards the interior of the solid, i.e. in at least one direction normal to the surface of the particle, especially in any direction normal to the surface of the particle, until it reaches a substantially constant value at the core of said particle.

The inventors have observed that the choice of metaldehyde and the variation of its proportion towards the interior of the solid, i.e. its distribution along a positive or negative gradient, towards the interior of the solid of the particle makes it possible to reduce the amount of solid, of particle and of bait consumed by the harmful molluscs for molluscicidal efficacy that is at least conserved.

In a molluscicidal particle according to the invention, the distribution of metaldehyde in a variable proportion towards the interior of the solid makes it possible to limit the consumption of solid of the particle by harmful molluscs to an external part of the particle while at the same time maintaining a high molluscicidal effect.

The inventors have found that varying the proportion of metaldehyde towards the interior of the solid makes it possible to kill harmful molluscs for an amount of solid ingested by said harmful molluscs that is reduced relative to a conventional solid, especially a solid with a constant proportion of metaldehyde towards the interior of said solid.

The inventors have found that varying the proportion of metaldehyde towards the interior of the solid results in stoppage of consumption of the particle by any first mollusc after the ingestion of only a fraction of the solid and before the death of said first mollusc, said ingested fraction of solid being lethal for said first mollusc. In addition, it turns out that it is possible to choose this distribution so that the stoppage of consumption makes it possible to leave a residual fraction of solid that can be consumed by at least a second mollusc (different from the first mollusc), said residual fraction being lethal for any other mollusc (different from the first mollusc) consuming said residual fraction.

Advantageously, the distribution of metaldehyde in the solid of a particle according to the invention is also chosen:
  to result in consumption by ingestion of an initial amount of solid by a mollusc, said initial amount being lethal for this mollusc,
  to induce stoppage of consumption of the solid by the mollusc after ingestion of said initial amount and before the death of the mollusc, and
  so as to leave a residual amount of solid that may be lethal to any other mollusc, different from said first mollusc, consuming at least part of the residual amount of solid.

Advantageously, the solid is chosen so that said initial amount is lethal to a harmful mollusc, the death of this harmful mollusc that has consumed said initial amount being delayed over time relative to the end of consumption of solid by the harmful mollusc.

Advantageously and according to the invention, the solid that is suitable for use as an ingested poison for harmful molluscs comprises an excipient (also named a support) that is edible and attractive to harmful molluscs. Advantageously, the solid comprises a major amount of the edible excipient and a minor amount of metaldehyde dispersed in the volume of the solid, with a variable proportion towards the interior of the solid.

Advantageously and according to the invention, the edible excipient is formed from a preparation chosen from the group formed by cereal flours, especially a durum wheat flour, a common wheat flour, a barley flour, a corn flour, a sorghum flour, cereal coproducts, protein-rich plant flours, oil-rich plant flours, tuber flours, for example potato flour.

A molluscicidal particle according to the invention is suitable for constituting, in a phase prior to ingestion and of start of ingestion of a part (surface) of the solid, a food that is attractive and appetizing to harmful molluscs. In the phase of ingestion by a mollusc, the ingested solid has a variable (increased or decreased) proportion of metaldehyde as the ingestion proceeds, such that the harmful mollusc stops ingesting the solid and then dies due to the effect of the combined ingestion of the amount of solid and of metaldehyde.

Advantageously and according to the invention, the proportion of metaldehyde varies in at least one direction normal to the surface of the particle, especially in any direction normal to the surface of the particle.

Advantageously and according to the invention, in certain embodiments, the particle may be a particle in the form of a platelet, a strip, a granule of substantially cubic shape or rotationally cylindrical shape along a main axial direction of elongation of the particle.

A particle of cylindrical shape has a longitudinal dimension (height of the cylinder) extending in the axial direction of elongation of the particle and a radial dimension (diameter of the cross section of the particle) extending perpendicular to the axial direction. In this embodiment, the height and diameter may be comparable values. It is also possible for the height value to be greater than the diameter value. It is then an elongated rod. It is, however, also possible for the length value to be less than the diameter value. It is then a particle of discoid shape. It is also possible for the cross section (or base) of the particle to be of any shape, for example of prismatic, polygonal, frustoconical or other shape. It may be a particle in the form of a cylinder having any base, especially an elliptical base.

In such a particle of cylindrical shape forming a granule according to the invention, the proportion of metaldehyde is constant along the longitudinal axis of each granule. On the other hand, the proportion of metaldehyde varies along the radial axis towards the interior of the solid.

Advantageously and according to the invention, in other embodiments, the particle is of substantially spherical shape and said proportion varies in any radial direction towards the interior of the solid. Such a substantially spherical or perfectly spherical [particle] has three dimensions extending in three mutually orthogonal directions and of the same order of magnitude and has a proportion of metaldehyde that is variable towards the interior of the solid and in at least one, especially in any, radial direction of the spherical particle until a substantially constant proportion value is reached at the core of said spherical particle.

Advantageously and according to the invention, since the particle is of spherical shape, the proportion of metaldehyde varies in a variation profile that is substantially identical in each radial direction. However, there is nothing to prevent the proportion of metaldehyde from varying in a different variation profile in each radial direction towards the interior of the solid.

Advantageously and according to certain embodiments of the invention, the proportion of metaldehyde varies, especially increases and/or decreases, continuously towards the interior of the solid. In these embodiments, the term "continuously" qualifying the variation of the proportion of metaldehyde towards the interior of the solid is understood in the mathematical sense.

In these embodiments according to the invention, the proportion of metaldehyde may vary in a variation rate (positive or negative) but constant rate (in the form of an affine function) towards the interior of the solid. In these embodiments according to the invention, the proportion of metaldehyde varies in a continuous variation rate.

However, there is nothing to prevent the proportion of metaldehyde from varying towards the interior of the solid successively in a plurality of segments (increasing or decreasing) of distinct affine functions. In these embodiments according to the invention, the proportion of metaldehyde then varies in a discontinuous variation rate.

In these embodiments according to the invention, there is nothing to prevent the proportion of metaldehyde from either being zero at the surface of the solid and increasing towards the interior of the solid or even decreasing between the surface and the interior of the solid until a substantially constant proportion value, especially zero, is reached at the core of said particle.

In these embodiments according to the invention, the proportion of metaldehyde may vary in a variation rate (positive or negative) but constant rate (in the form of an affine function) towards the interior of the solid, or in a variation rate (positive or negative) but variable rate, for example in the form of a function chosen from a polynomial function of degree different from 1, an exponential function, a logarithmic function, a trigonometric function or the like (function of random or any variation).

The variation of the proportion of metaldehyde towards the interior of the solid may be monotonous (in the mathematical sense of the term), i.e. the proportion of metaldehyde may be increasing towards the interior of the solid between the surface of the particle and the core of the particle, or may be decreasing towards the interior of the solid between the surface of the particle and the core of the particle. In this variant, the metaldehyde variation rate (gradient) remains positive or negative without changing sign, especially to a central zone of the particle in which the proportion of metaldehyde no longer varies.

Advantageously and according to the invention, the proportion of metaldehyde varies towards the interior of the solid over at least part of the volume of the solid. Advantageously, in certain embodiments according to the invention, the proportion of metaldehyde varies towards the interior of the solid only over part of the thickness of the solid.

Advantageously, in other embodiments of the invention, the proportion of metaldehyde varies discontinuously towards the interior of the solid. In these embodiments according to the invention, the particle according to the invention has a plurality of superposed solid layers, at least two consecutive superposed layers of solid being of different compositions, the proportion of metaldehyde being different between these two consecutive layers and towards the interior of the solid.

In these other embodiments according to the invention, there is nothing to prevent the proportion of metaldehyde from varying in at least one layer of solid and towards the interior of the solid.

Each of the superposed layers, in particular all the superposed layers, may have a constant thickness over the entire periphery of the particle. However, there is nothing to prevent at least one of the superposed layers from having a variable thickness in the volume of the particle. In addition, each of the superposed layers may have a relative thickness different from the thickness of another superposed layer.

Advantageously, in these other particular embodiments according to the invention, a particle, named a two-layer particle, may also have an outer surface layer with a mean proportion of metaldehyde in the surface layer and an inner core with a mean proportion of metaldehyde in the inner core inscribed within the outer surface layer and enveloped thereby, the mean proportion of metaldehyde in the surface layer being different (smaller or larger) relative to the mean proportion of metaldehyde in the inner core.

In these other particular embodiments according to the invention, the proportion of metaldehyde is constant towards the interior of the solid in the outer surface layer and in the inner core, the proportion of metaldehyde in the inner core being different (larger or smaller) from the proportion of metaldehyde in the outer surface layer.

Advantageously, in certain embodiments according to the invention, the proportion of metaldehyde increases towards the interior of the solid. The mean proportion of metaldehyde in the surface layer is less than the mean proportion of metaldehyde in the inner core. In particular, in these embodiments of the invention, the mean proportion of metaldehyde in the surface layer is zero.

However, there is nothing to prevent, in other embodiments of the invention, the proportion of metaldehyde from decreasing towards the interior of the solid. In this embodiment according to the invention, the mean proportion of metaldehyde in the surface layer is greater than the mean proportion of metaldehyde in the inner core, said mean proportion of metaldehyde in the inner core being zero.

Advantageously and according to the invention, the metallic compound is a metallic salt. Advantageously and according to the invention, the metallic compound is chosen from the group formed by iron acetate, iron chloride, iron phosphate, sodium iron phosphate, iron pyrophosphate, iron nitrate, iron sulfate, ammonium iron sulfate, ferroproteins, iron sulfides, iron citrate, iron glyceryl phosphates (iron glycerophosphate), iron choline citrate, ammonium iron citrate, iron fumarate, iron gluconate, iron lactate, iron-sucrose complexes, iron-fructose complexes, iron-dextrose complexes, iron succinate, iron tartrate, iron oxalate, iron ascorbate and iron aspartate.

Advantageously and according to the invention, the metallic compound is iron phosphate.

Advantageously, in the preferential embodiment of a molluscicidal particle according to the invention, at least one metallic compound is chosen from the group formed by ferrous iron(II) phosphate and ferric iron(III) phosphate. It may thus be ferrous iron(II) phosphate of formula $Fe_3(PO_4)_2$ and of No. 14940-41-1 in the "Chemical Abstract Service, CAS" classification. It may also be ferric iron(III) phosphate of formula $FePO_4 \cdot nH_2O$, in which n represents the number of water molecules associated with each ferric iron(III) phosphate molecule. The value of n may be equal to 0; it is then anhydrous ferric iron(III) phosphate (CAS 10045-86-0); it may be equal to 2; it is then ferric iron(III) phosphate dihydrate (CAS No. 13463-10-0); it may be equal to 4; it is then ferric iron(III) phosphate tetrahydrate (CAS No. 14940-41-1).

Ferrous iron(II) phosphate and/or ferric iron(III) phosphate may be in an amorphous form or in a crystalline form, i.e. having a signal on x-ray diffraction analysis. The iron phosphate may be in the form of crystals of orthorhombic or monoclinic lattice.

Advantageously, in the preferential embodiment according to the invention, the solid comprises ferric iron(III) phosphate as sole metallic compound.

Advantageously and according to the invention, the solid comprises at least one agent, named a complexing agent, chosen from the group formed by polyorganic acids, especially polyaminocarboxylic acids, preferably polyaminoacetic acids, polyaminosuccinic acids, polyaminoglutaric acids or polyaminoaspartic acids, salts of polyorganic acids, esters of polyorganic acids and mixtures in all proportions of at least two thereof. In particular, each complexing agent is a compound that is capable of modifying the availability of the metal of the metallic compound with respect to the harmful molluscs.

Advantageously and according to the invention, at least one complexing agent is chosen from the group formed by EDTA (ethylenediamine-N,N,N',N'-tetraacetic acid), Na$_2$Ca EDTA (disodium calcium salt of ethylenediamine-N,N,N',N'-tetraacetic acid), EDDS (ethylenediamine-N,N'-disuccinic acid), DTPA (diethylenetriamine-N,N,N',N',N''-pentaacetic acid), Na$_2$ DTPA (pentasodium salt of diethylenetriamine-N,N,N',N',N''-pentaacetic acid), GLDA (L-glutamic-N,N-diacetic acid), Na$_2$ GLDA (disodium salt of L-glutamic-N,N-diacetic acid), HEDTA (ethylenediamine-N-hydroxyethyl-N',N'-diacetic acid), Na$_3$ HEDTA (trisodium salt of ethylenediamine-N-hydroxyethyl-N',N'-diacetic acid), BAPTA (1,2-bis(2-aminophenoxy)ethane-N,N,N',N'-tetraacetic acid), AM BAPTA (acetoxymethyl ester of 1,2-bis(2-aminophenoxy)ethane-N,N,N',N'-tetraacetic acid), HEIDA (2-hydroxyethylamine-N,N-diacetic acid), Na$_2$ HEIDA (sodium 2-hydroxyethylamine-N,N-diacetate), NTA (nitrilo-N,N,N-triacetic acid), Na$_3$ NTA (trisodium salt of nitrilo-N,N,N-triacetic acid), (S,S)-propane-1,3-diamine-N,N'-disuccinic acid, triethylenetetraaminehexaacetic acid, 2-aminoethanesulfonic-N,N-diacetic acid, IDA (imino-N,N-diacetic acid), HIDS (hydroxyimino-N,N-disuccinic acid), Na$_4$ HIDS (tetrasodium salt of hydroxyimino-N,N-disuccinic acid), ADA (N-(2-acetamido)imino-N,N-diacetic acid), IDHA (N-dicarboxyethyl-D,L-aspartic acid), EGTA (ethylene glycol bis(2-aminoethyl ether)-N,N,N',N'-tetraacetic acid), (S,S)-2-hydroxy-1,3-propane-N,N'-disuccinic acid, (S,S)-2-hydroxy-1,3-propane-N,N'-diglutaric acid, N-cinnamoyl-n-2,3-xylylhydroxylamine, 1,1,1-tris(3-hydroxy-2-oxodihydro-1-pyridylpropoxymethyl)ethane, ammonium N,N-diethyldithiocarbamate, DMSA (dimercaptosuccinic acid), hydroxydimethylpyridone, tetramethoxydimethylphosphine-bipyridine, the mixture of curcumin and piperine, deferoxamine, citric acid, diethylglutaric acid, 8-hydroxyquinoline-5-sulfonic acid, 1-methylpyrrolidone, the hemicalcium salt of lactobionic acid, epigallocatechin 3-gallate, aspartic acid diethoxysuccinate, EDDPA (ethylenediaminedialkylphosphonic acid), EDTMP (ethylenediaminetetramethylenephosphonic acid), DTPMP (diethylenetriaminepentamethylenephosphonic acid), Na DTPMP (sodium salt of diethylenetriaminepentamethylenephosphonic acid), EDDCHA (ethylenediamine-N,N'-bis(5-carboxy-2-hydroxyphenylacetic acid)), EDDHA (ethylenediamine-N,N'-bis(2-hydroxyphenylacetic acid)), EDDHMA (ethylenediamine-N,N'-bis(o-hydroxy-p-methylphenylacetic acid), EDDHSA (ethylenediamine-N,N'-bis(o-hydroxy-p-sulfophenylacetic acid), GLUDA (N,N-diacetic glutamic acid), HEEDTA (ethylenediamine-N-hydroxyethyl-N,N'N'-triacetic acid), LED3A (ethylenediamine-N-lauric-N,N'N'-triacetic acid), CDTA (cyclohexyl-1,2-dinitro-N,N,N',N'-tetraacetic acid), MGDA (methylglycinediacetic acid), MIDA (methyliminodiacetic acid), O-Trensox (8-hydroxyquinoline and trimers thereof), AcAcs (acetylacetonates), isonicotinoyl salicylaldehyde hydrazone, (S,S)-1,2-ethylenediaminediglutaric acid, (S,S)-1,3-propanediaminediglutaric acid, enterochelin, EDDM (ethylenediaminedimalonic acid), EDDT (ethylenediaminediitartric acid), glutamic acid, aspartic acid, glycinamide-N,N-disuccinic acid, 1,2-diethyl-3-hydroxypyridin-4-one hydrochloride, 2-(2-(2-hydroxybenzyl)amino)ethylamino)-2-(2-hydroxyphenyl)acetic acid, 2-methyl-3-hydroxy-4-pyridine carboxylic acid, 3-hydroxy-4-pyridinecarboxylic acid, 3-hydroxy-4-pyridinecarboxylic acid, an alginate, a glycinate, glycine, hexadentate hydroxypyridinonate, hexadentate pyridinone, lignosulfonates, lipophilic aroylhydrazones, calcium(II) acetylacetonate, (1S,2S)-1,2-bis(2-hydroxyphenyl)ethylene, benzylhydroxamic alginic acids, catechol disulfonate, choline citrate, D-glucopyranosiduronic acids, amino acids, lysine, methylhydroxamic alginic acids, ethylenediamine-N,N'-bis(2-hydroxy-5-methylphenyl)-N,N'-diacetic acid, tetracyclic porphyrin, trencan, trishydroxypyridone, deferri-exochelin, ciclopirox olamine, ethylenediamine-N,N'-bis(2-hydroxy-5-methylbenzyl)-N,N'-diacetic acid (HJB), lysinates, L-aspartic-N,N-diacetic acid (ASDA), the tetrasodium salt of L-aspartic-N,N-diacetic acid (Na$_4$ ASDA), LTMP, tetraethylthiuram disulfide, phytic acid, silybin, gluconic acids, humic acids, Exjade®, 2-{2-[(2-hydroxybenzyl)amino]ethylamino}-2-{2-hydroxyphenyl}acetic acid (DCHA), chitin, chelain resin, deferroxamine, D-penicillamine, 2,3-dimercapto-1-propanol, 3-amino-1H-1,2,3-triazole, mellitic acid, pyridylmethylamine, 1-hydroxyethane-1,1-diphosphonic acid (HEDP) and aminotris(methylenesulfonic acid) (ATMP).

Advantageously and according to the invention, at least one metallic compound is present in the solid in a variable proportion, especially increasing or decreasing, towards the interior of the solid.

Advantageously and according to the invention, at least one complexing agent is present in the solid in a variable proportion, especially increasing or decreasing, towards the interior of the solid.

Advantageously and according to the invention, at least one complexing agent and at least one metallic compound have similar respective distributions, i.e. their respective proportions vary, especially increase or decrease, in the same direction of variation towards the interior of the solid.

Advantageously and according to the invention, the metallic compound, especially each metallic compound, is present in the solid in a mean mass proportion of between 0.1% and 10%, especially about 2%. The expression "mean mass proportion of metallic compound in the solid" means the mass of metallic compound relative to the mass of the corresponding solid.

Advantageously and according to the invention, metaldehyde is present in the solid of the particle in a mean mass proportion of between 0.2% and 5%, especially between 0.5% and 2%, in particular about 1%. The expression "mean mass proportion of metaldehyde in the solid" means the mass of metaldehyde relative to the mass of the corresponding solid.

Advantageously, the two-layer particle according to the invention is formed from an outer surface layer and an inner core inscribed within the outer surface layer and enveloped thereby, said outer surface layer and said inner core being formed from two solids containing different proportions of metaldehyde.

Advantageously and according to the invention, the solid of the outer surface layer constitutes from 15% to 50% and especially about 33% of the mass of the solid of the particle.

Such a particle thus comprises an inner core made of solid forming from 50% to 85% by mass of the particle and an outer surface layer, itself also made of solid, and coating the inner core and representing between 15% and 50% of the mass of the particle.

Advantageously, in certain embodiments of a two-layer particle according to the invention, the proportion of metaldehyde in the outer surface layer is less than the proportion of metaldehyde in the inner core.

Advantageously, in a two-layer particle according to these embodiments, the metallic compound, especially each metallic compound, is present in the solid of the outer surface layer in a mean mass proportion of between 1% and 10%, especially between 3% and 8%, particularly about 6%.

Advantageously, in a two-layer particle according to these embodiments, the metallic compound, especially each metallic compound, is present in the solid of the inner core of the particle in a substantially zero mass proportion.

In these embodiments of a two-layer particle according to the invention, the inner core of the particle is substantially free of metallic compound.

However, there is nothing to prevent the metallic compound, especially each metallic compound, from being present in the solid of the inner core of the particle in a mass proportion greater than the mass proportion of metallic compound in the outer surface layer.

Advantageously, in a two-layer particle according to these embodiments, metaldehyde is present in the solid of the inner core of the particle in a mean mass proportion of greater than 1%, especially between 1% and 5%, in particular between 1% and 2%, preferably about 1.5%. Such a proportion of metaldehyde is sufficient to limit the consumption of the particle by a harmful mollusc, but also to afford a synergistic molluscicidal effect with the metallic compound(s) and, where appropriate, in combination the complexing agent(s).

Advantageously, in a two-layer particle according to these embodiments, metaldehyde is present in the solid of the outer surface layer of the particle in a mass proportion of less than 0.2%, especially in a mass proportion that is detectable only in trace amount. Advantageously, according to these embodiments, the mass proportion of metaldehyde may be zero.

Advantageously, in a two-layer particle according to these embodiments of the invention, the outer surface layer is free of metaldehyde. The mass proportion of metaldehyde at the surface of the particle is zero. Thus, harmful molluscs ingesting a portion of solid of the outer surface of the particle according to the invention do not ingest metaldehyde during the initial phase of consumption by ingestion of the solid of said particle.

Advantageously, a two-layer particle according to these embodiments of the invention is formed as follows:
  the outer surface layer comprises iron phosphate and ethylenediamine-N,N,N',N'-tetraacetic acid (EDTA), said outer surface layer being free of metaldehyde; and
  the inner core comprises metaldehyde and is free of iron phosphate and of ethylenediamine-N,N,N',N'-tetraacetic acid (EDTA).

Advantageously, in these embodiments of a two-layer particle according to the invention:
  iron phosphate is present in the outer surface layer in a mass proportion of about 6%;
  metaldehyde is present in the inner core in a mass proportion of about 1.5%.

In other embodiments of a two-layer particle according to the invention, the proportion of metaldehyde in the outer surface layer is greater than the proportion of metaldehyde in the inner core.

Advantageously, in a two-layer particle according to these other embodiments of the invention, the metallic compound, especially each metallic compound, is present in the solid of the inner core in a mean mass proportion of between 1% and 5%, especially between 2% and 4%, particularly about 3%.

Advantageously, in a two-layer particle according to these other embodiments of the invention, the metallic compound, especially each metallic compound, is present in the solid of the outer surface layer of the particle in a substantially zero mass proportion. The outer surface layer of the particle is thus substantially free of metallic compound.

However, in these other embodiments of a two-layer particle according to the invention, there is nothing to prevent the metallic compound, especially each metallic compound, from being present in the solid of the outer surface layer of the particle in a mass proportion greater than the mass proportion of metallic compound in the inner core.

Advantageously, in a two-layer particle according to these other embodiments of the invention, metaldehyde is present in the solid of the surface layer of the particle in a mean mass proportion of between 1% and 10%, especially between 1% and 5%, preferably about 3%.

Advantageously, in a two-layer particle according to these other embodiments, metaldehyde is present in the solid of the inner core of the particle in a mass proportion of less than 0.2%, especially in a mass proportion that is detectable only in trace amount. Advantageously, according to these other embodiments, the mass proportion of metaldehyde may be zero.

Advantageously, in a two-layer particle according to these other embodiments of the invention, the outer surface layer is free of metallic compound. The mass proportion of metallic compound at the surface of the particle is zero.

Advantageously, in a two-layer particle according to these other embodiments of the invention:
  the outer surface layer comprises metaldehyde and is free of iron phosphate and of ethylenediamine-N,N,N',N'-tetraacetic acid (EDTA); and
  the inner core comprises iron phosphate and ethylenediamine-N,N,N',N'-tetraacetic acid (EDTA) and is free of metaldehyde.

Advantageously, in these other embodiments of a two-layer particle according to the invention:
  iron phosphate is present in the inner core in a mass proportion of about 3%; and
  metaldehyde is present in the outer surface layer in a mass proportion of about 3%.

Advantageously, in a two-layer particle according to all the embodiments of the invention, the outer surface layer and/or the inner core comprise(s) an amount of at least one excipient that is edible for harmful molluscs. Said edible excipient may be identical or different in the outer surface layer and the inner core.

The invention is also directed to a molluscicidal bait in divided form comprising at least one molluscicidal particle according to the invention.

Advantageously and according to the invention, the bait is in the form of a solid in divided form. The bait may be in the form of a particle composition according to the invention. Advantageously and according to the invention, each particle has a mean mass of between 5 mg and 500 mg.

The invention is also directed to the use of at least one particle according to the invention as a molluscicidal bait.

The invention is directed in particular to the use of a bait according to the invention for controlling harmful molluscs, especially gastropods, chosen from the group formed by:
  slugs, especially of the Limacidae family, of the Arionidae family and of the Milacidae family, more particularly of the species *Deroceras reticulatum*, of the species *Arion hortensis*, of the species *Arion ater agg* and of the species *Milax gagates*,
  land snails of the genera *Helix, Cernuel, Theba* and *Achatina*, more particularly of the species *Helix aspersa*, of the species *Cernuella virgata* and of the species *Theba pisana*; and water snails of the genera *Biomphalaria, Lynea* and *Pomacea*, especially *Pomacea canaliculata*.

The invention moreover covers a process for controlling harmful molluscs, in which an amount of bait according to the invention is provided to harmful molluscs.

Advantageously and according to the invention, the amount of bait corresponds to an authorized application dose of about 5 kg/ha in agriculture corresponding to a mass of iron phosphate spread per hectare of crop of about 150 g.

The invention also relates to a particle, to a molluscicidal bait comprising at least one such particle, to the use of such a particle as molluscicidal bait and to a process for controlling harmful molluscs, characterized in combination by all or some of the characteristics mentioned hereinabove or hereinbelow.

Other aims, characteristics and advantages of the invention will emerge on reading the description that follows and the non-limiting examples, which are given solely as illustrations of the invention.

Manufacture of the Baits by Coating

"Two-layer" particles according to the invention are formed via a two-step process in which a solid core is first formed, and said solid core is then coated with a coating composition to form the bait particles according to the invention.

Such a globular, especially substantially spherical, "two-layer" particle according to the invention is formed via any suitable process, for example by continuous or batch coating of a nucleus forming a core of the particle with compositions containing different proportions of metaldehyde. In particular, such a particle according to the invention is obtained, for example, by coating a nucleus forming the core of the particle and comprising metaldehyde with a composition free of metaldehyde and precursor of the solid of the outer surface layer of the particle.

1) Formation of the Solid Core by:
weighing out the various precursor ingredients of the solid core; and then
mixing the ingredients using a ribbon blender or an intensive blender;
incorporating water in vapour form or in liquid form and/or paraffin in an amount sufficient to form a continuous homogeneous paste;
compressing/extruding the paste through a die of an extruder/electric cooker;
fragmenting the strands of bait obtained so as to form unitary and individualized bait granules;
where appropriate, stabilizing the granules by cooling and drying in order to store them at room temperature.

2) Coating of the Solid Core
weighing out the various ingredients of the coating layer; and then
mixing the ingredients using a ribbon blender or an intensive blender;
placing the particles forming the solid core in a blender; and then
while blending, adding an amount of water so as to wet the outer surface of the solid cores and an amount of the ingredients of the coating layer in powder form so as to obtain adhesion of the powder to the surface of the solid core. This step is performed in a coating device known for its use in the coating of food preparations or seeds in agriculture. This coating step is repeated until the desired bait structure is obtained; and then
stabilizing the bait particles by suitable drying to allow storage of the baits at room temperature.

As a variant, a nucleus of organic or mineral nature is used, onto which is applied, by blending, a first layer comprising, for example, metaldehyde, followed by a second layer comprising iron phosphate. After drying, a bait is obtained formed from a nucleus, a first inner layer comprising metaldehyde and an outer surface layer comprising iron phosphate.

Manufacture of the Baits by Coextrusion

A "two-layer" particle of cylindrical shape is obtained according to the invention by coextrusion of a composite yarn formed from:
an inner core obtained from a composition having a first proportion of metaldehyde; and
an outer surface layer obtained from a composition having a second proportion of metaldehyde, which is different—less than or greater than—the first proportion, and coating the inner core;
followed by a step of chopping the composite yarn to form cylindrical particles in the form of rods or granules.

By way of example, the inner core may be formed from a composition having a first non-zero proportion of metaldehyde and the outer surface layer may be formed from a composition having a second proportion of metaldehyde which is lower—especially zero—than the first proportion.

Such "two-layer" particles according to the invention are formed by formation and superposition of the core and of the surface layer by coextrusion (preferably in twin-screw extruders) in one step starting with two precursor pasty compositions, of the inner core and of the outer surface layer, respectively;
weighing out the precursor ingredients of the solid core and of the coating layer; and then
mixing the precursor ingredients of the solid core using a ribbon blender or an intensive blender and incorporating water in vapour form or in liquid form and/or paraffin in an amount sufficient to form a continuous homogeneous paste;
mixing the precursor ingredients of the coating layer using a ribbon blender or an intensive blender and incorporating water in vapour form or in liquid form and/or paraffin in an amount sufficient to form a continuous homogeneous paste;
coextruding the precursor pastes of the core and of the coating layer through a coextrusion die using two extruders/electric cookers;
fragmenting the bait strands obtained so as to form unitary and individualized bait granules;
stabilizing the granules by cooling and drying so as to store them at room temperature.

Slug Populations

Wild adult slugs of homogeneous size are collected from agricultural plots favourable to the development of their population. These wild slugs are maintained under rearing conditions (temperature, humidity, lighting, ventilation and plant food) favourable to their development until the tests are performed.

Slug Mortality Under Controlled Conditions 25 test boxes each containing one slug are placed in an air-conditioned chamber maintained at a temperature of between 10° C. and 20° C., under a controlled atmosphere with a relative humidity of between 60% and 90% and under periodic lighting. A bait granule is placed in each test box. The slugs that are dead 3 and 8 days after placing the bait in the test box are counted over time. The amount of bait consumed by the slug in each box is noted. The cumulative mean mortality rate (CMMR, %) is calculated by counting the number of slugs killed over the period (in number of days) relative to the 25 starting slugs.

Slug Mortality Under Semi-Controlled Conditions

Tests under semi-controlled conditions are performed in external cages according to CEB protocol No. 48. 25 slugs are placed in a grated square cage covering a ground surface area of 1 m². The soil of the ground is worked so as to have a substantially flat and packed surface so as to avoid burying of the slugs. 10 to 20 lettuce plants are bedded out in the soil of each cage. A roofing tile forming a refuge for the slugs is placed in the centre of each cage. An amount of bait corresponding to the dose of bait applied per hectare is spread homogeneously over the surface of the ground in the cage. For example, 0.5 g of bait is applied per cage, corresponding to an applied bait dose of 5 kg/ha, or 0.7 g of bait is applied per cage, corresponding to an applied bait dose of 7 kg/ha. The dead slugs are counted periodically after the bait has been put in place.

EXAMPLE 1—COMPARATIVE TESTS OF THE TOXICITY OF THE BAITS ON GREY SLUGS (*DEROCERAS RETICULATUM*) UNDER CONTROLLED CONDITIONS

Tests on grey slugs are performed with the following baits:
bait free of active material ("control"),
control baits comprising metaldehyde in a mass proportion of 4% ("ME 4%") or of 2.5% ("ME 2.5%"). The "ME 4%" and "ME 2.5%" baits contain metaldehyde homogeneously distributed throughout the volume of the solid of the bait particles;
control ("FeP/EDTA") bait comprising iron phosphate in a mass proportion of 3% and EDTA (ethylenediamine-N,N,N',N'-tetraacetic acid) in an equimolar proportion with the iron of the iron phosphate. The ("FeP/EDTA") bait contains iron phosphate and EDTA distributed homogeneously throughout the volume of the solid of the bait particles;
control "FeP 1%/EDTA/ME 1%" and "FeP 2%/EDTA/ME 1%" baits comprising iron phosphate in a mass proportion of 1% and 2%, respectively, EDTA (ethylenediamine-N,N,N',N'-tetraacetic acid) in an equimolar proportion with the iron of the iron phosphate, and metaldehyde in a mass proportion of 1%. The "FeP 1%/EDTA/ME 1%" and "FeP 2%/EDTA/ME 1%" baits contain iron phosphate, EDTA and metaldehyde distributed homogeneously throughout the volume of the solid of the bait particles.

The above tests are performed as comparative tests:
a test performed with a two-layer bait (TL FeP 2%/EDTA/ME 1%) according to the invention comprising iron phosphate in a mass proportion of 2%, EDTA in an equimolar proportion with the iron of the iron phosphate, and metaldehyde in a mass proportion of 1%, and formed from an inner core comprising metaldehyde and from an outer surface layer comprising iron phosphate and EDTA, and
a test performed with a two-layer bait (TL ME 1%/FeP 2%/EDTA) according to the invention comprising iron phosphate in a mass proportion of 2%, EDTA in an equimolar proportion with the iron of the iron phosphate, and metaldehyde in a mass proportion of 1%, said bait being formed from an inner core comprising iron phosphate and EDTA, and an outer surface layer comprising metaldehyde.

The two-layer bait "TL FeP 2%/EDTA/ME 1%" according to the invention has an inner core forming about ⅔ of the volume of the bait and comprising the metaldehyde of the bait, and an outer surface layer forming about ⅓ of the volume of the bait and comprising the iron phosphate and the EDTA. The mass proportion of iron phosphate in the outer surface layer is then about 6%, the EDTA being present in the outer surface layer in equimolar proportion relative to the iron of the iron phosphate. The mass proportion of metaldehyde in the inner core is about 1.5%.

The two-layer bait "TL ME 1%/FeP 2%/EDTA" has an inner core forming about ⅔ of the volume of the bait and an outer surface layer forming about ⅓ of the volume of the bait. The mass proportion of metaldehyde in the outer surface layer is then about 3%. The mass proportion of iron phosphate in the inner core is about 3%, the EDTA being present in the inner core in equimolar proportion relative to the iron of the iron phosphate. In the two-layer bait ("TL ME 1%/FeP 2%/EDTA"), the proportion of metaldehyde decreases towards the interior of the solid.

The overall compositions of the baits described above are given in Table 1 below, in which the percentages are mass percentages relative to the total mass of the bait.

TABLE 1

| | Bait composition | | | |
|---|---|---|---|---|
| Bait | Wheat flour | Metal-dehyde | Iron phosphate | Fe/EDTA (mol) |
| Control | 100% | 0 | 0 | 0 |
| ME 4% | 96% | 4% | 0 | 0 |
| ME 2.5% | 97.5% | 2.5% | 0 | 0 |
| FeP/EDTA | 90.9% | 0 | 3% | 1 |
| FeP 1%/EDTA/ME 1% | 96% | 1% | 1% | 1 |
| FeP 2%/EDTA ME 1% | 93% | 1% | 2% | 1 |
| TL FeP 2%/EDTA/ME 1% | 96% | 1% | 1% | 1 |
| TL ME 1%/FeP 2%/EDTA | 96% | 1% | 1% | 1 |

The results of the toxicity tests performed three times are given in Table 2 below in which CMMR, % represents the cumulative mean mortality rate of the grey slugs and BC represents the mean value of the mass (in milligrams) of bait consumed by each slug.

TABLE 2

| | Test duration | | |
|---|---|---|---|
| | 3 days | 8 days | |
| Active material | CMMR, % | CMMR, % | BC, mg |
| Control | 0 | 3 | 18 |
| ME 4% | 10 | 81 | 6.72 |
| ME 2.5% | 6 | 72 | 7.57 |
| FeP/EDTA | 58 | 92 | 9.97 |
| FeP 1%/EDTA/ME 1% | 28 | 79 | 4.43 |
| FeP 2%/EDTA/ME 1% | 64 | 91 | 4.21 |
| TL FeP 2%/EDTA/ME 1% | 72 | 93 | 4.11 |
| TL ME 1%/FeP 2%/EDTA | 24 | 77 | 3.79 |

FeP = iron phosphate; ME = metaldehyde; EDTA = ethylenediamine-N,N,N',N'-tetraacetic acid; the percentages are mass percentages.

With the two-layer bait according to the invention, a CMMR, % value of 93% is observed at 3 days and at 8 days, which is higher than the CMMR, % value (92%) observed with the FeP/EDTA bait, but with an amount of bait according to the invention consumed by the slugs (4.11 mg) which is 2.4 times smaller than the amount (9.97 mg) of this control bait. A "two-layer" bait according to the invention has efficacy at 3 days and at 8 days that is improved for a reduced amount of bait consumed.

EXAMPLE 2—TOXICITY ON BLACK SLUGS (ARION HORTENSIS) UNDER CONTROLLED CONDITIONS

The results of toxicity tests performed three times under controlled conditions are given in Table 2 below, in which the CMMR, % represents the cumulative mean mortality rate of the black slugs and BC represents the mean value of the mass (in milligrams) of bait consumed by each black slug.

TABLE 3

| Active material | Test duration | | |
|---|---|---|---|
| | 3 days | 8 days | |
| in the bait | CMMR, % | CMMR, % | BC, mg |
| Control | 0 | 1 | 18.18 |
| ME 4% | 12 | 78 | 9.16 |
| ME 2.5% | 10 | 68 | 10.50 |
| FeP/EDTA | 14 | 80 | 9.21 |
| FeP 2%/EDTA/ME 1% | 11 | 79 | 7.95 |
| TL FeP 2%/EDTA/ME 1% | 27 | 91 | 7.57 |

By treating the slugs with the bait according to the invention (TL FeP 2%/EDTA/ME 1%), CMMR values at 3 days and at 8 days are obtained that are higher (27%, 91%) than the CMMR values at 3 days and at 8 days obtained with the FeP 2%/EDTA/ME 1% bait (11%, 79%), with the FeP/EDTA bait (14%, 80%) and with the ME 4% (12%, 78%) or ME 2.5% baits (10%, 68%). In addition, such an improved CMMR value is obtained with a mean amount (7.57 mg) of bait consumed (BC) by each slug that is smaller than the amount (7.95 mg) of FeP 2%/EDTA/ME 1% bait, than the amount (9.21 mg) of FeP/EDTA bait, than the amount (10.50 mg) of ME 2.5% bait and than the amount (9.16 mg) of ME 4% bait consumed by each slug.

The "two-layer" bait according to the invention has efficacy at 3 days and at 8 days that is improved for a reduced amount of bait consumed.

EXAMPLE 3—TOXICITY ON GREY SLUGS UNDER SEMI-CONTROLLED CONDITIONS

The results of the tests repeated five times are given in Table 4 below in which CMMR, % represents the cumulative mean mortality rate and AM (in g/ha) represents the mass (in grams) of active material (iron phosphate or metaldehyde or iron phosphate and metaldehyde) applied per hectare of treated surface.

TABLE 4

| | | Treatment duration | | | |
|---|---|---|---|---|---|
| | AM, | 4 days | | 8 days | |
| Active material | g/ha | CMMR, % | Ratio | CMMR, % | Ratio |
| Control | 0 | 8.8 | nd | 18 | nd |
| ME 4% | 200 | 61.6 | 0.308 | 73 | 0.365 |
| ME 2.5% | 125 | 58 | 0.464 | 70 | 0.56 |
| FeP/EDTA | 210 | 68.4 | 0.326 | 82 | 0.39 |
| FeP 2%/EDTA/ME 1% | 150 | 65 | 0.433 | 73 | 0.49 |
| TL FeP 2%/EDTA/ME 1% | 150 | 73.4 | 0.489 | 82 | 0.547 |

(nd: not defined)

By treating the slugs with the bait according to the invention ("TL FeP 2%/EDTA/ME 1%"), a cumulative mean mortality rate (CMMR, %) after 4 days and 8 days of treatment is obtained which is greater than or equal to (73.5% and 82%, respectively) the CMMR observed with the "FeP 2%/EDTA/ME 1%" bait (65% and 73%, respectively) and the CMMR observed with the "FeP/EDTA" bait (68.4% and 82%, respectively), but with an amount (150 g/ha) of active material (AM) applied that is smaller than the amount (210 g/ha) of active material of the "FeP/EDTA" bait. The "Ratio" columns of Table 4 show the CMMR, % values relative to the amount of active material (AM) applied and reflecting the improved efficacy of the bait according to the invention. These results demonstrate the advantage in terms of efficacy afforded by the "TL FeP 2%/EDTA/ME 1%" bait according to the invention relative to a bait in which the active material(s) has (have) a homogeneous distribution.

EXAMPLE 4—TOXICITY ON GREY SLUGS UNDER SEMI-CONTROLLED CONDITIONS

The results of the toxicity tests on slugs under semi-controlled conditions repeated three times are given in Table 5 below in which CMMR, % represents the cumulative mean mortality rate and AM (in g/ha) represents the mass (in grams) of active material (iron phosphate or metaldehyde or iron phosphate and metaldehyde) applied per hectare of treated surface.

TABLE 5

| | | Treatment duration | | | |
|---|---|---|---|---|---|
| | AM, | 4 days | | 8 days | |
| Active material in the bait | g/ha | CMMR, % | Ratio | CMMR, % | Ratio |
| Control | 0 | 2 | nd | 6 | nd |
| FeP/EDTA | 210 | 57 | 0.271 | 82 | 0.39 |
| FeP 2%/EDTA/ME 1% | 150 | 69 | 0.46 | 82 | 0.55 |
| TL FeP 2%/EDTA/ME 1% | 150 | 73 | 0.487 | 84 | 0.56 |

(nd: not defined)

By treating the slugs with the bait according to the invention "TL FeP 2%/EDTA/ME 1%", CMMR values at 4 days and at 8 days are obtained that are higher (73% and 84%, respectively) than the CMMR values observed with the homogeneous "FeP 2%/EDTA/ME 1%" bait (69% and 82%, respectively) and than the CMMR values observed with the "FeP/EDTA" bait (57% and 82%, respectively). These improved CMMR values are also obtained with amounts of applied active material (150 g/ha) that are smaller than the amount of active material (210 g/ha) applied with the "FeP/EDTA" bait. The "Ratio" columns of Table 5 show the values of the ratio between the cumulative mean mortality rate (in %) and the amount of active material applied, reflecting the efficacy of the bait. These results demonstrate the advantage in terms of efficacy afforded for a "two-layer" bait according to the invention.

EXAMPLE 5—TOXICITY ON BLACK SLUGS UNDER SEMI-CONTROLLED CONDITIONS

The results of the toxicity tests repeated twice are given in Table 6 below in which CMMR, % represents the cumulative mean mortality rate and AM (in g/ha) represents the mass (in grams) of active material (iron phosphate or metaldehyde or iron phosphate and metaldehyde) applied per hectare of treated surface.

TABLE 6

| Active material in the bait | AM, g/ha | Treatment duration | | | |
|---|---|---|---|---|---|
| | | 4 days | | 8 days | |
| | | CMMR, % | Ratio | CMMR, % | Ratio |
| Control | 0 | 2 | nd | 3 | nd |
| FeP/EDTA | 210 | 24 | 0.11 | 61 | 0.29 |
| FeP 2%/EDTA/ME 1% | 150 | 53 | 0.35 | 72 | 0.48 |
| TL FeP 2%/EDTA/ME 1% | 150 | 60 | 0.40 | 76 | 0.51 |

(nd: not defined)

On treating black slugs with the "TL FeP 2%/EDTA/ME 1%" bait according to the invention, CMMR values at 4 days and at 8 days are obtained that are higher (60% and 76%, respectively) than the CMMR values observed with the homogeneous "FeP 2%/EDTA/ME 1%" bait (53% and 72%, respectively) and with the "FeP/EDTA" bait (24% and 61%, respectively). Such an improvement in the molluscicidal efficacy is also obtained with an amount of applied bait according to the invention (150 g/ha) that is smaller than the amount (210 g/ha) of "FeP/EDTA" bait.

The "Ratio" columns of Table 6 show the CMMR, % values relative to the mass of active material (AM) applied and reflecting the efficacy of the bait. These results demonstrate the advantage afforded by a two-layer bait according to the invention on the treatment of harmful molluscs.

The invention claimed is:

1. A molluscicidal particle formed from a solid suitable for use as an ingested poison for harmful mollusks, said solid comprising metaldehyde and at least one metallic compound, the metallic compound comprising at least one metal selected from the group consisting of iron, copper, zinc and aluminum, wherein
the solid comprises metaldehyde in a proportion that increases towards the interior of said metaldehyde containing solid,
wherein the at least one metallic compound is present in the solid of the outer surface layer of the particle in a mass proportion greater than the mass proportion of metallic compound in the inner core, and wherein the distribution of metaldehyde in the solid of the particle being so chosen to yield an enhanced molluscicide efficiency against harmful mollusks consuming a molluscicide amount of said solid within a period of 3 days at the maximum following the onset of consumption of the solid by said harmful mollusks and affording a rapid protection of plants and crops against said harmful mollusks.

2. The molluscicidal particle according to claim 1 wherein,
the solid comprises metaldehyde in a proportion that varies discontinuously towards the interior of said metaldehyde containing solid,
the molluscicidal particle is formed from an outer surface layer and an inner core inscribed within the outer surface layer and enveloped thereby, said outer surface layer and said inner core being formed from two solids containing different proportions of metaldehyde,
the proportion of metaldehyde in the outer surface layer is less than the proportion of metaldehyde in the inner core, and
the at least one metallic compound is present in the solid of the outer surface layer of the particle in a mass proportion greater than the mass proportion of metallic compound in the inner core.

3. The particle according to claim 2, wherein the particle is of substantially spherical shape and said proportion of metaldehyde varies in any radial direction of the particle towards the interior of the solid.

4. The particle according to claim 2, wherein the at least one metallic compound is iron phosphate.

5. The particle according to claim 2, wherein the solid comprises at least one complexing agent selected from the group consisting of polyorganic acids, salts of polyorganic acids, esters of polyorganic acids and mixtures in all proportions of at least two thereof.

6. The particle according to claim 2, wherein:
the outer surface layer comprises iron phosphate and ethylenediamine-N,N,N',N'-tetraacetic acid (EDTA), said outer surface layer being free of metaldehyde; and
the inner core comprises metaldehyde and is free of iron phosphate and of ethylenediamine-N,N,N',N'-tetraacetic acid (EDTA).

7. The particle according to claim 6, wherein the iron phosphate is present in the outer surface layer in a mass proportion of about 6%, and the metaldehyde is present in the inner core in a mass proportion of about 1.5%.

8. A solid molluscicidal bait in divided form comprising at least one molluscicidal particle according to claim 2.

9. A process for controlling harmful mollusks, comprising providing an effective amount of the molluscidal bait according to claim 8 to harmful mollusks, said molluscicidal bait being in divided form comprising at least one molluscicidal particle formed from a solid suitable for use as an ingested poison for harmful mollusks, said solid comprising metaldehyde and at least one metallic compound, the metallic compound comprising at least one metal selected from the group consisting of iron, copper, zinc and aluminum, wherein
the solid comprises metaldehyde in a proportion that increases towards the interior of said metaldehyde containing solid, and
the distribution of metaldehyde in the solid of a particle being so chosen to yield an enhanced molluscicide efficiency against harmful mollusks consuming a molluscicide amount of said solid within a period of 3 days at the maximum following the onset of consumption of the solid by said harmful mollusks and affording a rapid protection of plants and crops against said harmful mollusks.

10. A molluscicidal particle formed from a solid suitable for use as an ingested poison for harmful mollusks, said solid comprising metaldehyde and at least one metallic compound, the metallic compound comprising at least one metal selected from the group consisting of iron, copper, zinc and aluminum, wherein the solid comprises metaldehyde in a proportion that increases towards the interior of said metaldehyde containing solid, wherein the at least one metallic compound is present in the solid of the outer surface layer of the particle in a mass proportion greater than the mass proportion of metallic compound in the inner core, and wherein the solid comprises metaldehyde in a proportion that varies continuously towards the interior of said solid.

11. A process for controlling harmful mollusks, comprising providing an effective amount of a molluscidal bait to harmful mollusks, said molluscicidal bait being in divided form comprising at least one molluscicidal particle formed from a solid suitable for use as an ingested poison for harmful mollusks, said solid comprising metaldehyde and at least one metallic compound, the metallic compound comprising at least one metal selected from the group consisting of iron, copper, zinc and aluminum, wherein the solid comprises metaldehyde in a proportion that varies discontinuously towards the interior of said metaldehyde containing solid, the molluscicidal particle is formed from an outer surface layer and an inner core inscribed within the outer surface layer and enveloped thereby, said outer surface layer and said inner core being formed from two solids containing different proportions of metaldehyde, the proportion of metaldehyde in the outer surface layer is less than the proportion of metaldehyde in the inner core, and the at least one metallic compound is present in the solid of the outer surface layer of the particle in a mass proportion greater than the mass proportion of metallic compound in the inner core, the distribution of metaldehyde in the solid of a particle being so chosen to yield an enhanced molluscicide efficiency against harmful mollusks consuming a molluscicide amount of said solid within a period of 3 days at the maximum following the onset of consumption of the solid by said harmful mollusks and affording a rapid protection of plants and crops against said harmful mollusks.

* * * * *